US00PP33861P2

(12) United States Plant Patent
Kobayashi

(10) Patent No.: US PP33,861 P2
(45) Date of Patent: Jan. 11, 2022

(54) **NEW GUINEA *IMPATIENS* PLANT NAMED 'DONGIWIROWHI 20'**

(50) Latin Name: *Impatiens hawkeri*
Varietal Denomination: Dongiwirowhi 20

(71) Applicant: DUMMEN GROUP B.V., De Lier (NL)

(72) Inventor: Ruth Kobayashi, Carlsbad, CA (US)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 17/230,955

(22) Filed: Apr. 14, 2021

(51) Int. Cl.
*A01H 5/02* (2018.01)
*A01H 6/16* (2018.01)

(52) U.S. Cl.
USPC ..... Plt./318.2
CPC ..... *A01H 6/16* (2018.05)

(58) Field of Classification Search
USPC ..... Plt./318.2
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Impatiens* plant named 'Dongiwirowhi 20' characterized by its upright to somewhat outwardly spreading and uniformly mounding plant habit; moderately vigorous growth habit; freely branching habit; glossy dark green-colored leaves;
freely flowering habit; semi-double flowers that are white in color; and good garden performance.

2 Drawing Sheets

Figure 1:
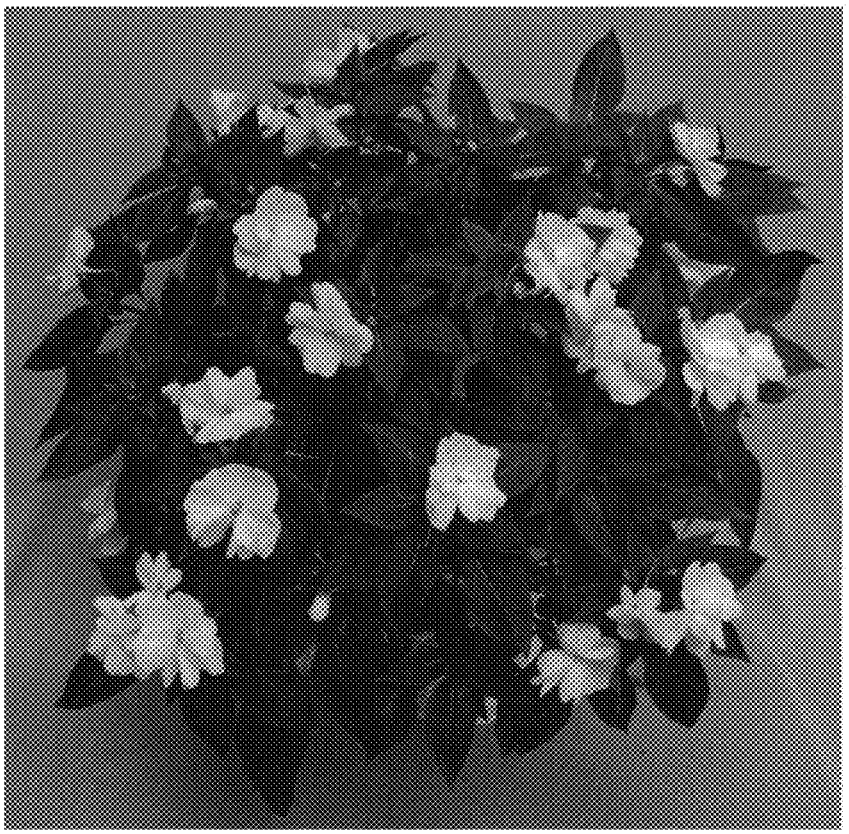

Botanical designation: *Impatiens hawkeri.*
Cultivar denomination: 'DONGIWIROWHI 20'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Dümmen Group B.V. of De Lier, The Netherlands on Oct. 29, 2020, application number 2020/2735. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of New Guinea *Impatiens* plant, botanically known as *Impatiens hawkeri* and hereinafter referred to by the name 'Dongiwirowhi 20'.

The new *Impatiens* plant is a product of a planned breeding program conducted by the Inventor in Koka, Ethiopia and Encinitas, Calif. The objective of the breeding program is to create new freely branching and early and freely flowering New Guinea *Impatiens* plants with attractive double flowers and good garden performance.

The new *Impatiens* plant originated from a cross-pollination made by the Inventor in November, 2016 in Koka, Ethiopia of a proprietary selection of *Impatiens hawkeri* identified as code number NN14-012710-005, not patented, as the female, or seed, parent with a proprietary selection of *Impatiens hawkeri* identified as code number NN-1322, not patented, as the male, or pollen, parent. The new *Impatiens* plant was discovered and selected by the Inventor as a single flowering plant from within the progeny of the stated cross-pollination in a controlled greenhouse environment in Encinitas, Calif. in April, 2017.

Asexual reproduction of the new *Impatiens* plant by terminal vegetative cuttings in a controlled greenhouse environment in Rheinberg, Germany since June, 2017 has shown that the unique features of this new *Impatiens* plant are stable and reproduced true to type in successive generations.

SUMMARY OF THE INVENTION

Plants of the new *Impatiens* have not been observed under all possible combinations of environmental conditions and cultural practices. The phenotype may vary somewhat with variations in environmental conditions such as temperature, daylight and light intensity without, however, any variance in genotype.

The following traits have been repeatedly observed and are determined to be the unique characteristics of 'Dongiwirowhi 20'. These characteristics in combination distinguish 'Dongiwirowhi 20' as a new and distinct *Impatiens* plant:

1. Upright to somewhat outwardly spreading and uniformly mounding plant habit.
2. Moderately vigorous growth habit.
3. Freely branching habit.
4. Glossy dark green-colored leaves.
5. Freely flowering habit.
6. Semi-double flowers that are white in color.
7. Good garden performance.

Plants of the new *Impatiens* can be compared to plants of the female parent selection. Plants of the new *Impatiens* differ primarily from plants of the female parent selection in flower color as flowers of plants of the new *Impatiens* are white in color whereas flowers of plants of the female parent selection are white tinged with pink in color.

Plants of the new *Impatiens* can be compared to plants of the male parent selection. Plants of the new *Impatiens* differ primarily from plants of the male parent selection in the following characteristics:

1. Plants of the new *Impatiens* have lighter green-colored leaves than plants of the male parent selection.
2. Plants of the new *Impatiens* have larger flowers than plants of the male parent selection.
3. Flowers of plants of the new *Impatiens* are white in color whereas flowers of plants of the male parent selection are light carmine and pinkish lavender bi-colored.

Plants of the new *Impatiens* can be compared to plants of *Impatiens hawkeri* 'Doimwirored', disclosed in U.S. Plant Pat. No. 31,564. In side-by-side comparisons, plants of the new *Impatiens* differ primarily from plants of 'Doimwirored' in the following characteristics:

1. Plants of the new *Impatiens* have smaller flowers than plants of 'Doimwirored'.
2. Flowers of plants of the new *Impatiens* are white in color whereas flowers of plants of 'Doimwirored' are dark red in color.

Plants of the new *Impatiens* can also be compared to plants of *Impatiens hawkeri* 'Moorea', disclosed in U.S. Plant Pat. No. 9,147. In side-by-side comparisons, plants of the new *Impatiens* differ primarily from plants of 'Moorea' in the following characteristics:

1. Plants of the new *Impatiens* are more vigorous than plants of 'Moorea'.
2. Plants of the new *Impatiens* have semi-double flowers whereas plants of 'Moorea' have single flowers.

BRIEF DESCRIPTION OF THE PHOTOGRAPHS

The accompanying colored photographs illustrate the overall appearance of the new *Impatiens* plant showing the colors as true as it is reasonably possible to obtain in colored reproductions of this type. Colors in the photographs may differ slightly from the color values cited in the detailed botanical description which accurately describe the colors of the new *Impatiens* plant.

The photograph on the first sheet (FIG. 1) is a side perspective view of a typical flowering plant of 'Dongiwirowhi 20' grown in a container.

Figure 2:
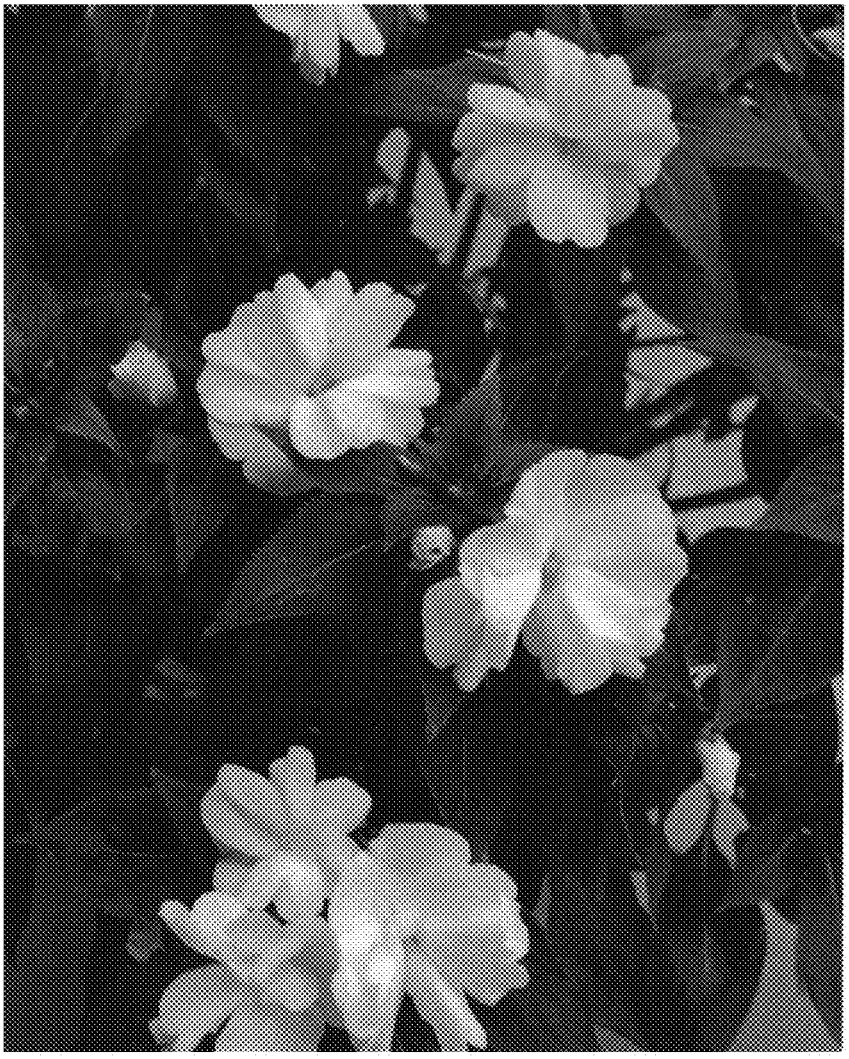

The photograph on the second sheet (FIG. 2) is a close-up view of a typical flowering plant of 'Dongiwirowhi 20'.

DETAILED BOTANICAL DESCRIPTION

The aforementioned photographs and following observations, measurements and values describe plants grown during the summer in 16.5-cm containers in a polyethylene-covered greenhouse in Encinitas, Calif. and under cultural practices typical of commercial New Guinea *Impatiens* production. During the production of the plants, day temperatures averaged 25° C., night temperatures averaged 20° C. and light levels ranged from 4,000 to 4,500 lux. Plants were 14 weeks old when the photographs and description were taken. In the following description, color references are made to The Royal Horticultural Society Colour Chart, 2015 Edition, except where general terms of ordinary dictionary significance are used.

Botanical classification: *Impatiens hawkeri* 'Dongiwirowhi 20'.

Parentage:

*Female, or seed, parent.*—Proprietary selection of *Impatiens hawkeri* identified as code number NN14-012710-005, not patented.

*Male, or pollen, parent.*—Proprietary selection of *Impatiens hawkeri* identified as code number NN-1322, not patented.

Propagation:

*Type.*—By terminal vegetative cuttings.

*Time to initiate roots, summer and winter.*—About five to seven days at day temperatures about 27° C. and night temperatures about 20° C.

*Time to produce a rooted young plant, summer and winter.*—About three weeks at day temperatures about 27° C. and night temperatures about 20° C.

*Root description.*—Fine, fibrous; typically white in color, actual color of the roots is dependent on substrate composition, water quality, fertilizers, substrate temperature and age of roots.

*Rooting habit.*—Freely branching; dense.

Plant description:

*Plant and growth habit.*—Upright to somewhat outwardly spreading and uniformly mounding plant habit; broad inverted triangle in overall shape; freely branching habit; bushy and dense appearance; moderately vigorous growth habit and moderate growth rate; strong and sturdy plants.

*Plant height.*—About 28.5 cm.

*Plant diameter.*—About 46 cm.

Lateral branch description:

*Branching habit.*—Freely branching with about five to seven primary lateral branches each with multiple secondary branches.

*Length.*—About 26 cm.

*Diameter.*—About 1.4 cm.

*Internode length.*—About 8 cm to 11 cm.

*Strength.*—Strong, flexible.

*Aspect.*—Initially upright to about 45° from vertical.

*Texture and luster.*—Smooth, glabrous; moderately glossy.

*Color, developing and developed.*—Close to 144A.

Leaf description:

*Arrangement.*—Typically in whorls or opposite; simple; leaves are durable.

*Length.*—About 8.5 cm.

*Width.*—About 3.75 cm.

*Shape.*—Broadly ovate to elliptic.

*Apex.*—Acuminate.

*Base.*—Attenuate.

*Margin.*—Serrate with ciliation.

*Texture and luster, upper surface.*—Smooth, glabrous; coriaceous; moderately glossy.

*Texture and luster, lower surface.*—Smooth, glabrous; coriaceous; slightly glossy.

*Venation pattern.*—Pinnate; arcuate.

*Color.*—Developing leaves, upper surface: Darker green than 147A. Developing leaves, lower surface: Close to 147B. Fully expanded leaves, upper surface: Darker green than between 147A and N189A; mid-vein, proximally, close to 144A to 144B, and distally, close to 147A; and lateral venation, darker green than between 147A and N189A. Fully expanded leaves, lower surface: Darker green than 147B; midvein, proximally, close to 144A to 144B, and distally, close to 144A; and lateral venation, close to 146A.

*Petiole length*.—About 3.25 cm.

*Petiole diameter*.—About 3 mm.

*Petiole texture and luster, upper and lower surfaces*.—Smooth, glabrous; moderately glossy.

*Petiole color, upper and lower surfaces*.—Close to 144A to 144B.

Flower description:

*Flower type and flowering habit*.—Semi-double axillary flowers that are rounded to slightly rectangular in shape; freely flowering habit, typically about four to six flower buds and opened flowers per lateral branch; flowers are positioned above and beyond the foliar plane, flowers typically face mostly upright to outwardly to slightly nodding.

*Flower longevity*.—Flowers typically last about four to seven days on the plant under greenhouse conditions; petals self-cleaning, gynoecium persistent.

*Fragrance*.—None detected.

*Natural flowering season*.—Year-round under greenhouse conditions; in the garden, flowering from spring until fall in California; early flowering habit, plants typically begin flowering about ten weeks from unrooted cuttings.

*Flower buds*.—Length: About 1.1 cm. Diameter: About 7 mm. Shape: Ovoid. Texture and luster: Smooth, glabrous; glossy. Color: Close to 144A to 144B.

*Flower diameter*.—About 5.2 cm by 5.7 cm.

*Flower depth*.—About 2.2 cm.

*Petals*.—Quantity and arrangement: Typically eight to ten in two whorls; if ten petals are present, there are one banner petal, two lateral petals and two lower petals per whorl. Timer and outer whorls: Length, banner petal: About 3 cm. Length, lateral petals: About 3 cm. Length, lower petals: About 3 cm. Width, banner petal: About 3.6 cm. Width, lateral petals: About 2.6 cm. Width, lower petals: About 2.6 cm. Shape, banner petal: Broadly obcordate. Shape, lateral and lower petals: Roughly cordate. Apex, all petals: Emarginate, partially notched. Base, all petals: Attenuate. Margin, all petals: Entire, moderately undulate. Texture and luster, all petals, upper and lower surfaces: Smooth, glabrous; slightly glossy; iridescent. Color, all petals: When opening and fully opened, upper surface: Close to NN155D; venation, close to NN155D; color becoming closer to NN155D variably tinged with close to 144A. When opening and fully opened, lower surface: Close to NN155D; venation, close to NN155D; banner midvein, close to 144A; color becoming closer to NN155D variably tinged with close to 144A.

*Sepals*.—Quantity and arrangement: Three in a single whorl; two laterals are opposite and the third modified into an elongated spur. Lateral sepal length: About 4 mm. Lateral sepal width: About 4 mm. Lateral sepal shape: Broadly deltoid to ovate. Lateral sepal apex: Acuminate. Lateral sepal base: Truncate. Lateral sepal margin: Entire, not undulate. Lateral sepal texture and luster, upper and lower surfaces: Smooth, glabrous; slightly glossy. Lateral sepal color, upper surface: Close to 144B to 144C. Lateral sepal color, lower surface: Close to 144A to 144B. Spurred sepal length (not including spur): About 1.2 cm. Spurred sepal width (proximally): About 1.2 cm. Spurred sepal shape (proximally): Broadly ovate. Spurred sepal base: Truncate. Spurred sepal margin (proximally): Entire, not undulate. Spurred sepal texture and luster (proximally), upper and lower surfaces: Smooth, glabrous; slightly glossy. Spurred sepal color (proximally), upper and lower surfaces: Close to NN155D; at the apex, close to 144A. Spur length: About 3.2 cm. Spur diameter: At flower, about 2 mm; at apex, less than 1 mm. Spur shape: Acicular, curved. Spur texture and luster: Smooth, glabrous; glossy. Spur color: Close to NN155D variably tinged with close to 144A.

*Peduncles*.—Length: About 3.7 cm. Diameter: About 2.5 mm. Angle: About 45° to 90° from vertical. Strength: Strong; flexible. Texture and luster: Smooth, glabrous; glossy. Color: Close to 144A.

*Reproductive organs*.—To date, reproductive organs have not been observed on plants of the new *Impatiens*. Seeds and fruits: To date, seed and fruit production has not been observed on plants of the new *Impatiens*.

Pathogen & pest resistance: To date, plants of the new *Impatiens* have not been observed to be resistant to pathogens and pests common to *Impatiens* plants.

Garden performance: Plants of the new *Impatiens* have been observed to have good garden performance and tolerate temperatures ranging from about 5° C. to about 40° C.

It is claimed:

1. A new and distinct *Impatiens* plant named 'Dongiwirowhi 20' as illustrated and described.

* * * * *